(12) United States Patent
Govari et al.

(10) Patent No.: US 8,475,450 B2
(45) Date of Patent: Jul. 2, 2013

(54) DUAL-PURPOSE LASSO CATHETER WITH IRRIGATION

(75) Inventors: Assaf Govari, Haifa (IL); Athanassios Papaioannou, Los Angeles, CA (US); Christopher Beeckler, Brea, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 481 days.

(21) Appl. No.: 12/345,720

(22) Filed: Dec. 30, 2008

(65) Prior Publication Data

US 2010/0168548 A1 Jul. 1, 2010

(51) Int. Cl.
*A61B 18/18* (2006.01)
*A61B 5/04* (2006.01)

(52) U.S. Cl.
USPC .............................................. 606/41; 600/374

(58) Field of Classification Search
USPC ................... 600/372, 374, 381, 393; 606/32, 606/37, 39, 41; 607/115–116, 119–120, 122–125
See application file for complete search history.

(56) References Cited

U.S. PATENT DOCUMENTS

| | | | |
|---|---|---|---|
| 3,971,364 A | 7/1976 | Fletcher | |
| 4,488,561 A | 12/1984 | Doring | |
| 4,764,114 A | 8/1988 | Jeffcoat | |
| 4,856,993 A | 8/1989 | Maness | |
| 4,917,102 A | 4/1990 | Miller et al. | |
| 4,917,104 A | 4/1990 | Rebell | |
| 5,263,493 A * | 11/1993 | Avitall | 607/122 |
| 5,368,564 A | 11/1994 | Savage | |
| 5,391,199 A | 2/1995 | Ben Haim | |
| 5,487,757 A | 1/1996 | Truckai | |
| 5,499,542 A | 3/1996 | Morlan | |
| 5,558,091 A | 9/1996 | Acker | |
| 5,563,354 A | 10/1996 | Kropp | |
| 5,643,197 A | 7/1997 | Brucker et al. | |
| 5,662,124 A | 9/1997 | Wilk | |
| 5,673,695 A | 10/1997 | McGee | |
| 5,680,860 A | 10/1997 | Imran | |
| 5,685,878 A | 11/1997 | Falwell | |
| 5,730,127 A | 3/1998 | Avitall | |
| 5,769,843 A | 6/1998 | Abela | |
| 5,820,591 A | 10/1998 | Thompson et al. | |

(Continued)

FOREIGN PATENT DOCUMENTS

DE 19750441 6/1999
EP 856292 A 8/1998

(Continued)

OTHER PUBLICATIONS

EP Search Report No: EP 09 25 2918 Dated Aug. 13, 2010.

(Continued)

*Primary Examiner* — Linda Dvorak
*Assistant Examiner* — Brian M Antiskay
(74) *Attorney, Agent, or Firm* — William A. Schoneman

(57) ABSTRACT

Cardiac catheters, including a lasso catheter, are provided for use in a system for electrical mapping of the heart has an array of raised, perforated electrodes, which are in fluid communication with an irrigating lumen. There are position sensors on a distal loop section and on a proximal base section of the catheter. The electrodes are sensing electrodes that may be adapted for pacing or ablation. The raised electrodes securely contact cardiac tissue, forming electrical connections having little resistance.

32 Claims, 5 Drawing Sheets

U.S. PATENT DOCUMENTS

| | | |
|---|---|---|
| 5,826,576 A | 10/1998 | West |
| 5,836,894 A | 11/1998 | Sarvazyan |
| 5,860,920 A | 1/1999 | McGee et al. |
| 5,860,974 A * | 1/1999 | Abele .............................. 606/41 |
| 5,865,815 A | 2/1999 | Tihon |
| 5,871,523 A | 2/1999 | Fleischman et al. |
| 5,902,248 A | 5/1999 | Millar |
| 5,916,147 A | 6/1999 | Boury |
| 5,938,694 A | 8/1999 | Jaraczewski et al. |
| 5,944,022 A | 8/1999 | Nardella |
| 5,964,757 A | 10/1999 | Ponzi |
| 5,974,320 A | 10/1999 | Ward |
| 5,983,126 A | 11/1999 | Wittkampf |
| 6,002,955 A | 12/1999 | Willems et al. |
| 6,048,329 A | 4/2000 | Thompson |
| 6,063,022 A | 5/2000 | Ben-Haim |
| 6,064,902 A | 5/2000 | Haissaguerre et al. |
| 6,123,699 A | 9/2000 | Webster, Jr. |
| 6,171,277 B1 | 1/2001 | Ponzi |
| 6,177,792 B1 | 1/2001 | Govari |
| 6,183,463 B1 | 2/2001 | Webster, Jr. |
| 6,198,974 B1 | 3/2001 | Webster, Jr. |
| 6,201,387 B1 | 3/2001 | Govari |
| 6,201,487 B1 | 3/2001 | Park |
| 6,203,493 B1 | 3/2001 | Ben Haim |
| 6,216,027 B1 | 4/2001 | Willis |
| 6,226,542 B1 | 5/2001 | Reisfeld |
| 6,239,724 B1 | 5/2001 | Doron |
| 6,241,724 B1 | 6/2001 | Fleischman |
| 6,267,781 B1 | 7/2001 | Tu |
| 6,272,371 B1 | 8/2001 | Ben-Haim |
| 6,272,672 B1 | 8/2001 | Conway |
| 6,301,496 B1 | 10/2001 | Reisfeld |
| 6,332,089 B1 | 12/2001 | Acker et al. |
| 6,335,617 B1 | 1/2002 | Osadchy |
| 6,371,955 B1 | 4/2002 | Fuimaono et al. |
| 6,436,059 B1 | 8/2002 | Zanelli |
| 6,456,864 B1 | 9/2002 | Swanson |
| 6,468,260 B1 | 10/2002 | Bumbalough et al. |
| 6,484,118 B1 | 11/2002 | Govari |
| 6,500,167 B1 | 12/2002 | Webster, Jr. |
| 6,522,933 B2 | 2/2003 | Nguyen |
| 6,551,302 B1 | 4/2003 | Rosinko |
| 6,574,492 B1 | 6/2003 | Ben Haim |
| 6,584,856 B1 | 7/2003 | Biter |
| 6,592,581 B2 | 7/2003 | Bowe |
| 6,602,242 B1 * | 8/2003 | Fung et al. .................... 604/528 |
| 6,612,992 B1 | 9/2003 | Hossack |
| 6,618,612 B1 | 9/2003 | Acker et al. |
| 6,669,692 B1 | 12/2003 | Nelson et al. |
| 6,690,963 B2 | 2/2004 | Ben-Haim et al. |
| 6,695,808 B2 | 2/2004 | Tom |
| 6,711,429 B1 | 3/2004 | Gilboa |
| 6,712,815 B2 | 3/2004 | Sampson et al. |
| 6,723,094 B1 | 4/2004 | Desinger |
| 6,727,371 B2 | 4/2004 | Müller |
| 6,814,733 B2 | 11/2004 | Schwartz |
| 6,835,173 B2 | 12/2004 | Couvillon, Jr. |
| 6,892,091 B1 | 5/2005 | Ben-Haim et al. |
| 6,908,464 B2 | 6/2005 | Jenkins et al. |
| 6,911,019 B2 | 6/2005 | Mulier et al. |
| 6,915,149 B2 | 7/2005 | Ben Haim |
| 6,945,956 B2 | 9/2005 | Waldhauser |
| 6,964,205 B2 | 11/2005 | Papakostas |
| 6,973,339 B2 | 12/2005 | Govari |
| 6,997,924 B2 | 2/2006 | Schwartz et al. |
| 7,008,401 B2 | 3/2006 | Thompson et al. |
| 7,008,418 B2 | 3/2006 | Hall et al. |
| 7,077,823 B2 | 7/2006 | McDaniel |
| 7,156,816 B2 | 1/2007 | Schwartz et al. |
| 7,235,070 B2 * | 6/2007 | Vanney ........................... 606/41 |
| 7,285,119 B2 | 10/2007 | Stewart et al. |
| 7,306,593 B2 | 12/2007 | Keidar |
| 7,311,704 B2 | 12/2007 | Paul |
| 7,397,364 B2 | 7/2008 | Govari |
| 7,419,489 B2 | 9/2008 | Vanney et al. |
| 7,481,774 B2 | 1/2009 | Brockway |
| 7,517,349 B2 | 4/2009 | Truckai et al. |
| 7,536,218 B2 | 5/2009 | Govari |
| 7,604,605 B2 | 10/2009 | Zvuloni |
| 7,681,432 B2 | 3/2010 | Hay |
| 7,686,767 B2 | 3/2010 | Maschke |
| 8,066,702 B2 | 11/2011 | Rittman et al. |
| 8,083,691 B2 | 12/2011 | Goldenberg |
| 2001/0047129 A1 | 11/2001 | Hall |
| 2001/0047133 A1 | 11/2001 | Gilboa |
| 2002/0002329 A1 * | 1/2002 | Avitall ........................... 600/377 |
| 2002/0022839 A1 | 2/2002 | Stewart et al. |
| 2002/0065455 A1 | 5/2002 | Ben-Haim et al. |
| 2002/0068866 A1 | 6/2002 | Zikorus |
| 2002/0165461 A1 | 11/2002 | Hayzelden |
| 2002/0193781 A1 | 12/2002 | Loeb |
| 2003/0105453 A1 | 6/2003 | Stewart et al. |
| 2003/0120195 A1 | 6/2003 | Milo |
| 2003/0130615 A1 | 7/2003 | Tom |
| 2003/0158494 A1 | 8/2003 | Dahl |
| 2003/0216722 A1 | 11/2003 | Swanson |
| 2004/0049255 A1 | 3/2004 | Jain |
| 2004/0064024 A1 | 4/2004 | Sommer |
| 2004/0068178 A1 | 4/2004 | Govari |
| 2004/0082948 A1 | 4/2004 | Stewart et al. |
| 2004/0097806 A1 | 5/2004 | Hunter |
| 2004/0102769 A1 | 5/2004 | Schwartz |
| 2004/0143175 A1 | 7/2004 | Coleman et al. |
| 2004/0147920 A1 | 7/2004 | Keidar |
| 2004/0152974 A1 | 8/2004 | Solomon et al. |
| 2004/0244464 A1 | 12/2004 | Hajdukiewicz |
| 2004/0254458 A1 | 12/2004 | Govari |
| 2005/0004565 A1 | 1/2005 | Vanney |
| 2005/0010095 A1 | 1/2005 | Stewart et al. |
| 2005/0033135 A1 | 2/2005 | Govari |
| 2005/0070894 A1 | 3/2005 | McClurken |
| 2005/0080429 A1 | 4/2005 | Freyman |
| 2005/0187544 A1 | 8/2005 | Swanson et al. |
| 2005/0277875 A1 | 12/2005 | Selkee |
| 2006/0009690 A1 | 1/2006 | Fuimaono |
| 2006/0009735 A1 | 1/2006 | Viswanathan |
| 2006/0015096 A1 | 1/2006 | Hauck |
| 2006/0020264 A1 | 1/2006 | Crowley et al. |
| 2006/0106295 A1 | 5/2006 | Jais et al. |
| 2006/0173480 A1 | 8/2006 | Zhang |
| 2006/0200049 A1 | 9/2006 | Leo |
| 2006/0235381 A1 | 10/2006 | Whayne et al. |
| 2006/0247618 A1 | 11/2006 | Kaplan |
| 2006/0253116 A1 | 11/2006 | Avitall et al. |
| 2007/0021742 A1 | 1/2007 | Viswanathan |
| 2007/0060832 A1 | 3/2007 | Levin |
| 2007/0060847 A1 | 3/2007 | Leo |
| 2007/0100332 A1 | 5/2007 | Paul |
| 2007/0106114 A1 | 5/2007 | Sugimoto |
| 2007/0142749 A1 | 6/2007 | Khatib |
| 2007/0151391 A1 | 7/2007 | Larkin |
| 2007/0156114 A1 | 7/2007 | Worley |
| 2007/0161882 A1 | 7/2007 | Pappone |
| 2007/0179492 A1 | 8/2007 | Pappone |
| 2007/0185397 A1 | 8/2007 | Govari |
| 2007/0191829 A1 | 8/2007 | McGee |
| 2007/0197939 A1 | 8/2007 | Wallace |
| 2007/0282211 A1 | 12/2007 | Ofek |
| 2008/0009750 A1 | 1/2008 | Aeby |
| 2008/0015568 A1 | 1/2008 | Paul |
| 2008/0051704 A1 | 2/2008 | Patel |
| 2008/0065111 A1 | 3/2008 | Blumenkranz |
| 2008/0071267 A1 | 3/2008 | Wang |
| 2008/0077049 A1 | 3/2008 | Hirshman |
| 2008/0097394 A1 | 4/2008 | Lampropoulos et al. |
| 2008/0161774 A1 | 7/2008 | Hastings et al. |
| 2008/0161795 A1 | 7/2008 | Wang et al. |
| 2008/0183075 A1 | 7/2008 | Govari |
| 2008/0249522 A1 | 10/2008 | Pappone et al. |
| 2008/0255540 A1 | 10/2008 | Selkee |
| 2008/0275428 A1 | 11/2008 | Tegg |
| 2008/0275442 A1 | 11/2008 | Paul |
| 2008/0275465 A1 | 11/2008 | Paul |
| 2008/0281319 A1 | 11/2008 | Paul |
| 2008/0287777 A1 | 11/2008 | Li |
| 2008/0288038 A1 | 11/2008 | Paul |

| | | | | | | |
|---|---|---|---|---|---|---|
| 2008/0294144 | A1 | 11/2008 | Leo | EP | 2289408 A | 3/2011 |
| 2008/0294158 | A1 | 11/2008 | Pappone | EP | 2338411 A1 | 6/2011 |
| 2009/0010021 | A1 | 1/2009 | Smith | EP | 2338412 A1 | 6/2011 |
| 2009/0093806 | A1 | 4/2009 | Govari | EP | 2130508 B1 | 12/2011 |
| 2009/0138007 | A1 | 5/2009 | Govari | JP | 2005345215 A | 12/2005 |
| 2009/0158511 | A1 | 6/2009 | Maze | JP | 2006064465 A | 3/2006 |
| 2009/0254083 | A1 | 10/2009 | Wallace et al. | WO | WO 95/10326 A1 | 4/1995 |
| 2009/0287118 | A1 | 11/2009 | Malek | WO | WO9510326 A1 | 4/1995 |
| 2009/0306650 | A1 | 12/2009 | Govari | WO | WO 96/05768 A1 | 2/1996 |
| 2010/0030209 | A1 | 2/2010 | Govari et al. | WO | WO9605768 A1 | 2/1996 |
| 2010/0063478 | A1 | 3/2010 | Selkee | WO | WO9729678 A2 | 8/1997 |
| 2010/0137845 | A1 | 6/2010 | Ramstein | WO | WO9729709 A1 | 8/1997 |
| 2010/0152574 | A1 | 6/2010 | Erdman | WO | WO9729710 A1 | 8/1997 |
| 2010/0168620 | A1 | 7/2010 | Klimovitch | WO | WO9729678 A3 | 9/1997 |
| 2010/0168918 | A1 | 7/2010 | Zhao | WO | WO9829032 A1 | 7/1998 |
| 2010/0222859 | A1 | 9/2010 | Govari et al. | WO | WO 99/56812 A | 11/1999 |
| 2011/0054287 | A1 | 3/2011 | Schultz | WO | WO03020139 A2 | 3/2003 |
| 2011/0054446 | A1 | 3/2011 | Schultz | WO | WO03020139 A3 | 8/2003 |
| 2011/0130648 | A1 | 6/2011 | Beeckler | WO | WO 2006/003216 A | 1/2006 |
| 2011/0144639 | A1 | 6/2011 | Govari et al. | WO | WO2006029563 A1 | 3/2006 |
| 2011/0160719 | A1 | 6/2011 | Govari et al. | WO | WO2006086152 A2 | 8/2006 |
| 2011/0184406 | A1 | 7/2011 | Selkee | WO | WO2006092563 A1 | 9/2006 |
| 2012/0053403 | A1 | 3/2012 | Ducharme et al. | WO | WO2007025230 A2 | 3/2007 |
| 2012/0143088 | A1 | 6/2012 | Schultz | WO | WO2007050960 A2 | 5/2007 |
| 2012/0172703 | A1 | 7/2012 | Esguerra et al. | WO | WO2007067938 A2 | 6/2007 |
| 2013/0006238 | A1 | 1/2013 | Ditter et al. | WO | WO2007082216 A1 | 7/2007 |
| | | | | WO | WO2007025230 A3 | 8/2007 |
| | | FOREIGN PATENT DOCUMENTS | | WO | WO2007098494 A1 | 8/2007 |
| EP | 1042990 A | 10/2000 | | WO | WO2007111182 A1 | 10/2007 |
| EP | 1181896 A | 2/2002 | | WO | WO2006086152 A3 | 11/2007 |
| EP | 1 502 555 A1 | 2/2005 | | WO | WO2007050960 A3 | 12/2007 |
| EP | 1586281 A1 | 10/2005 | | WO | WO2007067938 A3 | 12/2007 |
| EP | 1690564 A1 | 8/2006 | | WO | WO2006086152 B1 | 1/2008 |
| EP | 1743575 A2 | 1/2007 | | WO | WO2009078280 A1 | 6/2009 |
| EP | 928601 B1 | 4/2007 | | WO | WO2009085470 A1 | 7/2009 |
| EP | 1743575 A3 | 5/2007 | | WO | WO2009147399 A1 | 12/2009 |
| EP | 1 820 464 A1 | 8/2007 | | WO | WO 2010/008975 A2 | 1/2010 |
| EP | 1897581 A2 | 3/2008 | | | | |
| EP | 1897581 A3 | 6/2008 | | | | |
| EP | 2000789 A1 | 12/2008 | | | | |
| EP | 2000789 A2 | 12/2008 | | | | |
| EP | 2000789 A9 | 3/2009 | | | | |
| EP | 1586281 B1 | 4/2009 | | | | |
| EP | 1690564 B1 | 4/2009 | | | | |
| EP | 2047797 A2 | 4/2009 | | | | |
| EP | 2047797 A3 | 9/2009 | | | | |
| EP | 2127604 A1 | 12/2009 | | | | |
| EP | 2130508 A2 | 12/2009 | | | | |
| EP | 1743575 B1 | 1/2010 | | | | |
| EP | EP2130508 A3 | 1/2010 | | | | |
| EP | 2000789 A4 | 3/2010 | | | | |
| EP | 2171240 A2 | 4/2010 | | | | |
| EP | 1743575 B8 | 5/2010 | | | | |
| EP | 2229904 A | 9/2010 | | | | |
| EP | 2289403 A | 3/2011 | | | | |

OTHER PUBLICATIONS

Biter. W.J. et al., "Magnetic Wire Strain Sensor", 33$^{rd}$ International Sampe Technical Conference, Nov. 2001, vol. 33, pp. 12-23, Seattle, WA.

Biter, W.J. et al., "Magnetic Wire for Monitoring Strain in Composites", Sensors, Jun. 2001, www.sensormag.com, pp. 110-114.

Okumura, Y. et al. A Systematic Analysis of In Vivo Contact Forces on Virtual Catheter Tip-Tissue Surface Contact During Cardiac Mapping and Intervention. J of Cardiovasc Electrophysiol, vol. 19, pp. 632-640, Jun. 2008.

European Search Report, dated Jan. 9, 2013, for European Patent Application No. 11163281.6.

U.S. Appl. No. 13/760,335, filed Feb. 6, 2013, Govari et al.

* cited by examiner

DUAL-PURPOSE LASSO CATHETER WITH IRRIGATION

FIELD OF THE INVENTION

This invention relates to cardiac mapping and ablation systems. More particularly, this invention relates to a lasso catheter for use in a cardiac mapping and ablation system.

BACKGROUND OF THE INVENTION

Cardiac arrhythmia, such as atrial fibrillation, occurs when regions of cardiac tissue abnormally conduct electric signals to adjacent tissue, thereby disrupting the normal cardiac cycle and causing asynchronous rhythm. Important sources of undesired signals are located in the tissue region along the pulmonary veins of the left atrium and in the superior pulmonary veins. In this condition, after unwanted signals are generated in the pulmonary veins or conducted through the pulmonary veins from other sources, they are conducted into the left atrium where they can initiate or continue arrhythmia.

Procedures for treating arrhythmia include surgically disrupting the origin of the signals causing the arrhythmia, as well as disrupting the conducting pathway for such signals. More recently, it has been found that by mapping the electrical properties of the endocardium and the heart volume, and selectively ablating cardiac tissue by application of energy, it is sometimes possible to cease or modify the propagation of unwanted electrical signals from one portion of the heart to another. The ablation process destroys the unwanted electrical pathways by formation of non-conducting lesions.

In this two-step procedure—mapping followed by ablation—electrical activity at points in the heart is typically sensed and measured by advancing a catheter containing one or more electrical sensors into the heart, and acquiring data at a multiplicity of points. These data are then utilized to select the target areas at which ablation is to be performed.

U.S. Pat. No. 6,063,022 to Ben-Haim, which is assigned to the assignee of the present patent application and is incorporated herein by reference, describes an invasive probe including two position sensors in a fixed, known relation to the distal end of the probe. The position sensors generate signals responsive to their respective position coordinates and at least one contact sensor along a radial surface of the probe for generating a signal representing its contact with body tissue to be ablated by electrodes on the probe.

U.S. Pat. No. 6,272,371 to Ben-Haim, which is assigned to the assignee of the present patent application and is incorporated herein by reference, describes an invasive probe including a flexible portion that assumes a predetermined curve form when a force is applied thereto. Two position sensors, fixed to the distal portion of the probe in known positions, are used to determine position and orientation coordinates of at least one of the sensors, and to determine the locations of a plurality of points along the length of the distal portion of the probe.

PCT Patent Publication Wo 96/05768 and corresponding U.S. Patent Application Publication 2002/0065455 to Ben-Haim et al., which are assigned to the assignee of the present patent application and which are incorporated herein by reference, describe a system that generates six-dimensional position and orientation information regarding the tip of a catheter. This system uses a plurality of sensor coils adjacent to a locatable site in the catheter, for example near its distal end, and a plurality of radiator coils fixed in an external reference frame. These coils generate signals in response to magnetic fields generated by the radiator coils, which signals allow for the computation of six position and orientation dimensions, so that the position and orientation of the catheter are known without the need for imaging the catheter.

A lasso catheter is disclosed in commonly assigned U.S. Pat. No. 6,973,339, which is herein incorporated by reference. The lasso catheter is particularly adapted for pulmonary vein mapping and ablation. This catheter comprises: a curved section having a first position sensor that is capable of generating fewer than six dimensions of position and orientation information, one or more electrodes, adapted to measure an electrical property of the pulmonary vein; and a base section attached to a proximal end of the curved section. Disposed on the base section within 3 mm of the distal end thereof is a second position sensor, capable of generating six dimensions of position and orientation information.

SUMMARY OF THE INVENTION

Lasso catheters are generally used for ablating tissue along an arc surrounding an anatomical structure, such as the ostium of a pulmonary vein. Conventionally, the curved section or loop of the lasso catheter is generally thin and "floppy," for purposes of maneuverability, while ring electrodes disposed on the lasso are relatively large in order to minimize electrical resistance.

Embodiments of the present invention provide a lasso catheter that may be used for both ablation and sensing, and which has other advantageous features. Its distal curved portion, sometimes referred to herein as a "loop" or "loop segment", is typically thicker and stiffer than that of conventional lasso catheters. Rather than ring electrodes, the lasso catheter has relatively small, raised protuberant electrodes. The small size of these electrodes is advantageous in permitting measurement of local electrical activity with good spatial resolution. The bulges of the electrodes increase the surface area that is in contact with the heart tissue, and thus reduces the electrical resistance when the electrodes are used for ablation.

In order to provide local cooling and prevent adhesion during ablation, the electrodes may be fenestrated by multiple perforations. The perforations are in fluid contact with a lumen, which carries irrigation fluid from within the catheter to the outer surfaces of the electrodes and thence to the adjacent tissues. Another lumen may contain wires connected to each of the electrodes.

An embodiment of the invention provides a catheter, including an insertion tube and a resilient distal section fixed to the distal end of the insertion tube. The distal section has an inner irrigating lumen and a plurality of electrodes that bulge above the outer surface. The electrodes have a plurality of perforations formed therethrough, and the outer surface is in fluid communication with the irrigating lumen via the perforations.

According to an aspect of the catheter, the insertion tube is configured for insertion through a blood vessel into a heart of a subject, and wherein the resilient distal section defines an open loop when deployed within the heart.

An embodiment of the invention provides a method for locating an arrhythmogenic area in a heart of a living subject, The method is further carried out by inserting a catheter into a chamber of the heart, the catheter including an insertion tube and a resilient distal section that has an inner irrigating lumen and is fixed to the distal end of the insertion tube. The distal section also includes a plurality of electrodes that bulge above the outer surface, the electrodes having a plurality of perforations formed therethrough. The outer surface of the distal section is in fluid communication with the irrigating lumen via the perforations, The method is further carried out by locating the catheter in proximity to a target in the chamber, analyzing electrical signals received from the target via the catheter to make a determination that the electrical signals are indicative of abnormal electrical conduction within the heart, and responsively to the determination, conducting energy into the heart to thereby affect the abnormal electrical conduction.

BRIEF DESCRIPTION OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily always needed for practicing the present invention. In this instance, well-known circuits, control logic, and the details of computer program instructions for conventional algorithms and processes have not been shown in detail in order not to obscure the general concepts unnecessarily.

Figure 1:
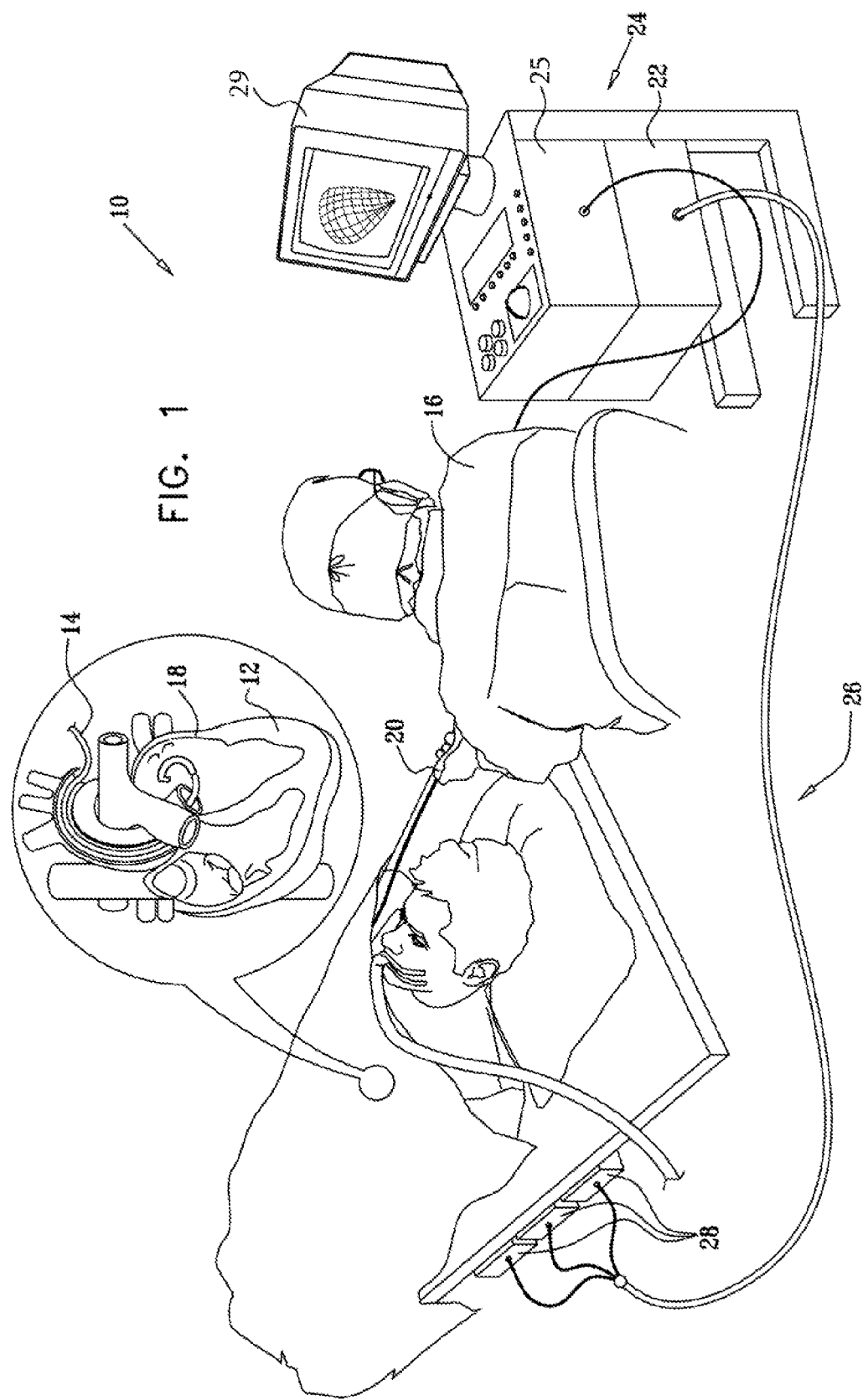
FIG. 1 is a pictorial illustration of a system for detecting areas of abnormal electrical activity and performing ablative procedures on a heart of a living subject in accordance with a disclosed embodiment of the invention.

Turning now to the drawings, reference is initially made to FIG. 1, which is a pictorial illustration of a system 10 for detecting areas of abnormal electrical activity and performing ablative procedures on a heart 12 of a living subject in accordance with a disclosed embodiment of the invention. The system comprises a lasso catheter 14, which is percutaneously inserted by an operator 16, who is typically a physician, through the patient's vascular system into a chamber or vascular structure of the heart. The operator 16 brings the catheter's distal tip 18 into contact with the heart wall at a target site that is to be evaluated. Electrical activation maps are then prepared, according to the methods disclosed in the above-noted U.S. Pat. Nos. 6,226,542, and 6,301,496, and in commonly assigned U.S. Pat. No. 6,892,091, whose disclosure is herein incorporated by reference.

Areas determined to be abnormal by evaluation of the electrical activation maps can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. Alternatively, other known methods of applying ablative energy can be used, e.g., ultrasound energy, as disclosed in U.S. Patent Application Publication No. 2004/0102769, whose disclosure is herein incorporated by reference. The principles of the invention can be applied to different heart chambers, and to mapping in sinus rhythm, and when many different cardiac arrhythmias are present.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a positioning processor 22, located in a console 24. The console 24 typically contains an ablation power generator 25. The catheter 14 may be adapted to conduct ablative energy to the heart using any known ablation technique, e.g., radiofrequency energy, ultrasound energy, and laser energy. Such methods are disclosed in commonly assigned U.S. Pat. Nos. 6,814,733, 6,997,924, and 7,156,816, which are herein incorporated by reference.

The positioning processor 22 is an element of a positioning system 26 that measures location and orientation coordinates of the catheter 14. Throughout this patent application, the term "location" refers to the spatial coordinates of the catheter, and the term "orientation" refers to its angular coordinates. The term "position" refers to the full positional information of the catheter, comprising both location and orientation coordinates.

In one embodiment, the positioning system 26 comprises a magnetic position tracking system that determines the position and orientation of the catheter 14. The positioning system 26 generates magnetic fields in a predefined working volume its vicinity and senses these fields at the catheter. The positioning system 26 typically comprises a set of external radiators, such as field generating coils 28, which are located in fixed, known positions external to the patient. The coils 28 generate fields, typically electromagnetic fields, in the vicinity of the heart 12.

In an alternative embodiment, a radiator in the catheter 14, such as a coil, generates electromagnetic fields, which are received by sensors (not shown) outside the patient's body.

Some position tracking systems that may be used for this purpose are described, for example, in the above-noted U.S. Pat. No. 6,690,963, and in commonly assigned U.S. Pat. Nos. 6,618,612 and 6,332,089, and U.S. Patent Application Publications 2004/0147920, and 2004/0068178, whose disclosures are all incorporated herein by reference. Although the positioning system 26 shown in FIG. 1 uses magnetic fields, the methods described below may be implemented using any other suitable positioning system, such as systems based on electromagnetic fields, acoustic or ultrasonic measurements. The positioning system 26 may be realized as the CARTO XP EP Navigation and Ablation System, available from Biosense Webster, Inc., 3333 Diamond Canyon Road, Diamond Bar, Calif. 91765.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by the sensors 31, 33 and a plurality of sensing electrodes 35. The digitized signals are received and used by the console 24 to compute the position and orientation of the catheter 14 and to analyze the electrical signals from the electrodes. The information derived from this analysis is used to generate an electrophysiological map of at least a portion of the heart 12 or structures such as the pulmonary venous ostia, for diagnostic purposes such as locating an arrhythmogenic area in the heart or to facilitate therapeutic ablation.

Typically, the system 10 includes other elements, which are not shown in the figures for the sake of simplicity. For example, the system 10 may include an electrocardiogram (ECG) monitor, coupled to receive signals from one or more body surface electrodes, so as to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. By comparing the position of the catheter 14 to that of the reference catheter, the coordinates of catheter 14 are accurately determined relative to the heart 12, irrespective of heart motion. Alternatively, any other suitable method may be used to compensate for heart motion.

Figure 2:
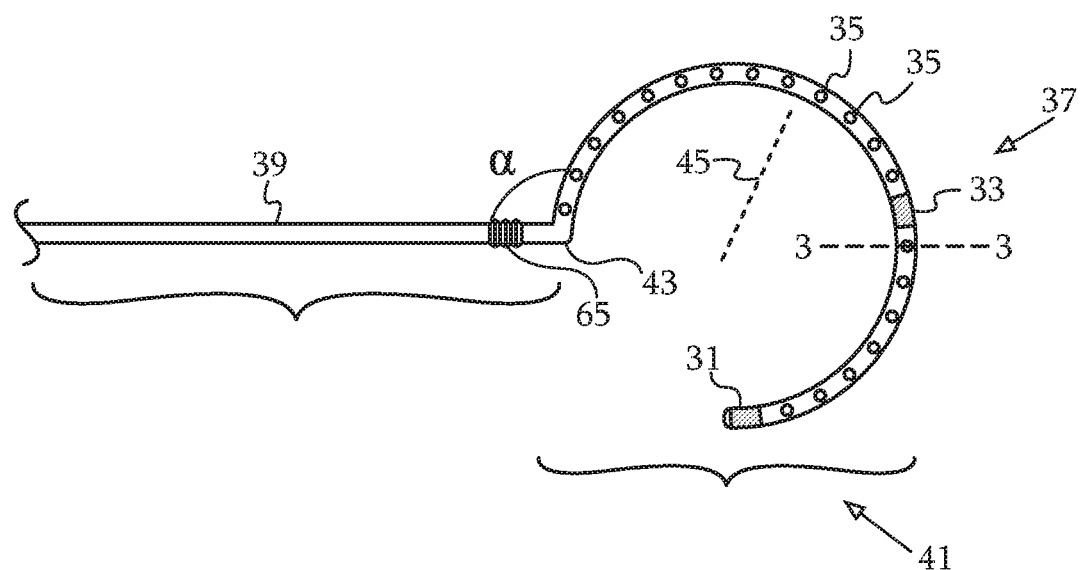
FIG. 2 is a side elevation of a lasso catheter that is constructed and operative in accordance with a disclosed embodiment of the invention.

Reference is now made to FIG. 2, which is a side elevation of a lasso catheter 37 that is constructed and operative in accordance with a disclosed embodiment of the invention. The catheter 37 is a steerable device. Its handle, control and steering mechanisms (not shown) are conventional and are omitted from FIG. 2 for simplicity. The catheter 37 features a base segment 39, which is bendable responsively to forces applied by the steering mechanisms. A distal curved section, referred to herein as loop segment 41, completes the lasso configuration. The loop segment 41 is joined to the base segment 39 by a range-restricted angle α at a joint 43. The angle α between the loop segment 41 and the base segment 39 optimally is about 90 decrees. The joint 43 may define a point where two initially-separate members (base segment 39; loop segment 41) are joined, or, alternatively, the joint 43 may define a point on the catheter 37 where a single member is bent, so as to form the base segment 39 and the loop segment 41. The loop segment 41 is of a known fixed length, having a curvature dimensioned to a particular medical application. The curvature may be adjustable using the steering and control mechanisms (not shown) of the catheter. A radius 45 of adjustable between 7-15 mm is suitable for cardiac applications. However, the radius 45 may vary up to 25 mm in some applications. In any case, the loop segment 41 may be dimensioned so as to conform to structures such as the ostia of pulmonary veins or the coronary sinus.

The loop segment 41 is constructed of a material that preferably is twistable but not stretchable when subjected to typical forces encountered in medical practice. Preferably, the loop segment 41 is sufficiently resilient so as to assume a predetermined curved form, i.e., an open circular or semicircular form when no force is applied thereto, and to be deflected from the predetermined curved form when a force is applied thereto. Preferably, the loop segment 41 has an elasticity that is generally constant over at least a portion of its length, for example, because of internal reinforcement of the curved section with a resilient longitudinal member, as is known in the art. The loop segment 41 is generally thicker and stiffer than conventional lassos. For example, the loop segment 41 may be made from polyurethane and be at least one mm in diameter.

Figure 3:
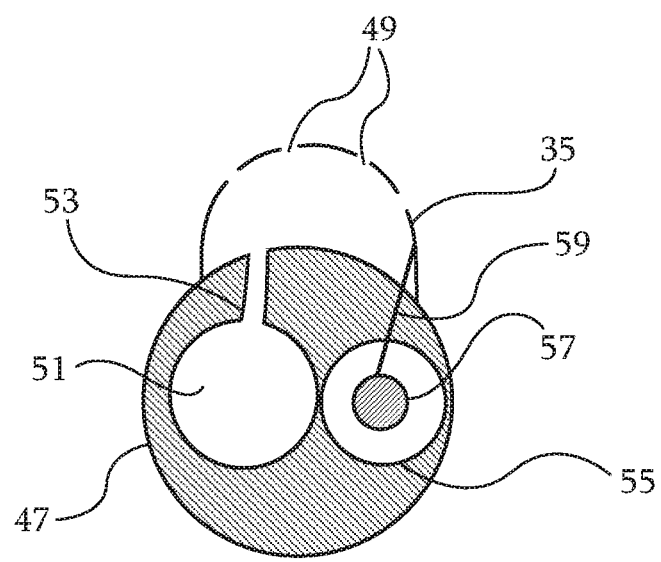
FIG. 3 is a cross section through the catheter shown in FIG. 2 taken through line 3-3.

One or more electrodes 35, adapted for sensing electrical characteristics of cardiac tissue, are fixed to the loop segment 41. Reference is now made to FIG. 3, which is a cross section through the catheter 37 (FIG. 2) taken through line 3-3, illustrating one of the electrodes 35. The electrodes 35 may bulge between about 0.1-0.5 mm above the outer surface 47 and have a generally rounded profile, forming a cap on the surface 47. In some embodiments the electrodes 35 may have a larger bulge, up to 1 mm above the surface. The electrodes 35 may extend over 25-270 percent of the circumference of the surface 47, as contrasted with a conventional ring electrode, which covers 100% of the circumference. The electrodes 35 may have a circular border. Alternatively, they may be elliptical in contour, as further described below. These configurations provide substantial contact between the electrodes 35 and the cardiac tissue, lowering electrical resistance as compared with conventional electrodes. The electrodes 35 may be 2-5 mm in dimension. The electrodes 35 may also be used for ablation, in which case the reduced electrical resistance is particularly advantageous. In one embodiment, two of the electrodes 35 are selected for performing bi-polar ablation, e.g., radiofrequency ablation in which case a cable 57 may include wires individually leading to the electrodes 35.

The exterior surface of the electrodes 35 is fenestrated by multiple small perforations 49 formed therethrough. Typically there are between 1 and 50 perforations having diameters of 0.05-0.4 mm. The perforations 49 are in fluid communication with an irrigating lumen 51 through a channel 53. A second lumen 55 carries cable 57 comprising one or more electrically conductive wires that link the electrodes 35 to the console 24 (FIG. 1), for example wire 59. The lumen 55 may also conduct additional wires as described below.

Figure 4:
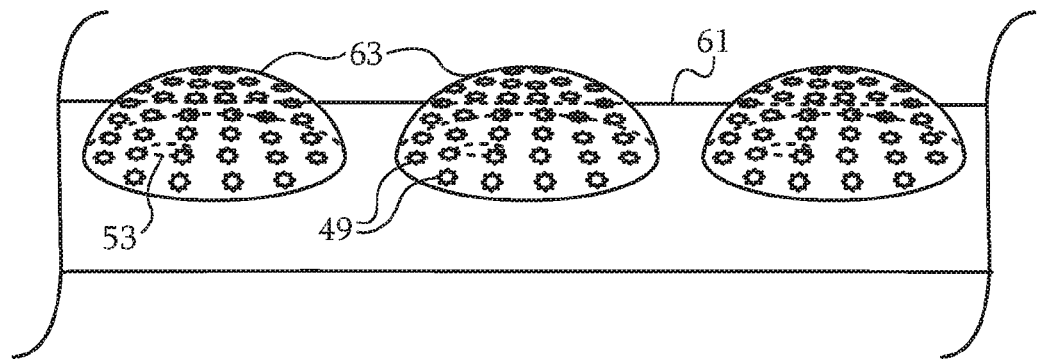
FIG. 4 a fragmentary elevational view of the shaft of a catheter that is constructed and operative in accordance with a disclosed embodiment of the invention.

Reference is now made to FIG. 4, which is a fragmentary elevational view of a shaft 61 of a catheter that is constructed and operative in accordance with a disclosed embodiment of the invention. Electrodes 63 are circular in contour, and the surface distribution of perforations 49 is substantially uniform.

Reverting to FIG. 2, at least a first single-coil position sensor 31 is fixed to loop segment 41. Preferably, the sensor 31 is fixed to the distal end of the loop segment 41 (distal with respect to the base segment 39), and a second single-coil position sensor 33 is fixed to the approximate center of the loop segment 41. Optionally, one or more additional single-coil position sensors (not shown) are fixed to the loop segment 41. Additionally, a multi-coil position sensor 65 is preferably fixed near the distal end of the base segment 39, in the vicinity of the joint 43, typically within 10 mm of the distal end. The sensor 65 is preferably able to generate six position and orientation dimensions, using techniques described in the above-cited PCT Patent Publications to Ben-Haim et al., or other techniques known in the art. The sensor 65 preferably comprises two or three coils, which are generally sufficient for generating six dimensions of position information. The sensors 31, 33 are preferably able to generate five position and orientation dimensions. A preferred electromagnetic mapping sensor is manufactured by Biosense Webster (Israel) Ltd., (Tirat Hacarmel, Israel) and marketed under the trade designation NOGA™. Alternatively, the sensors 31, 33, 65 comprise field sensors other than coils, such as Hall effect devices or other antennae, in which case the sensors 31, 33 are preferably smaller than the sensor 65.

The sensors 31, 33, 65 are fixed to the catheter 37 by any suitable method, for example, using polyurethane glue or the like. The sensors 31, 33, 65 are electrically connected to the cable 57 (FIG. 3), which extends through the catheter body and into a control handle (not shown) of the catheter 37. The cable 57 preferably comprises multiple wires encased within a plastic covered sheath. Within the catheter body, the cable 57 may be enclosed within a protective sheath along with wire 59 (FIG. 3). Preferably, in the control handle, the wires of the sensor cable are connected to a circuit board (not shown), which amplifies the signals received from the position sensors and transmits them to a computer housed in the console 24 (FIG. 1), in a form understandable to the computer. Alternatively, amplifying circuitry is included at the distal end of catheter 37, so as to reduce the effect of noise.

Reference is again made to FIG. 1. In order to use the position sensors 31, 33, 65, the subject is placed in a magnetic field that is generated, for example, by situating under the subject a pad containing field generator coils 28 for generating a magnetic field. A reference electromagnetic sensor (not shown) is preferably fixed relative to the subject, e.g., taped to the subject's back, and the catheter 37 is advanced into the subject's heart and into a desired location in or near one of the cardiac chambers, for example one of the pulmonary veins. Reverting now to FIG. 2, the coils in the sensors 31, 33, 65 generate weak electrical signals indicative of their position in the magnetic field. Signals generated by both the fixed reference sensor and the sensors 31, 33, 65 sensors in the heart are amplified and transmitted to coils 28 (FIG. 1), which analyzes the signals so as to facilitate the determination and visual display of the precise location of the sensors 31, 33, 65 relative to the reference sensor.

Each of the sensors 31, 33 preferably comprises one coil, and the sensor 65 preferably comprises three non-concentric, typically mutually orthogonal coils, such as those described in the above-cited PCT Patent Publication Wo 96/05768. The coils sense magnetic fields generated by the coils 28, which are driven by driver circuits in the generator 25 (FIG. 1). Alternatively, the sensors may generate fields, which are detected by fixed sensing coils (not shown), in which case the coils 28 can be omitted. The system 10 thus achieves continuous generation of five dimensions of position and orientation information with respect to each of the sensors 31, 33, and six dimensions with respect to position the sensor 65.

Figure 5:
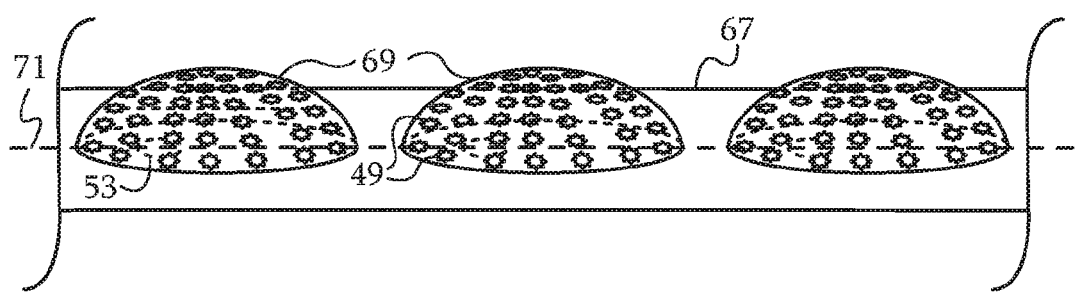
FIG. 5 is a fragmentary elevational view of the shaft of a catheter that is constructed and operative in accordance with an alternate embodiment of the invention.

Reference is now made to FIG. 5, which is a fragmentary elevational view of a shaft 67 of a catheter that is constructed and operative in accordance with an alternate embodiment of the invention. Electrodes 69 are elliptical in contour. The longitudinal axis 71 of the shaft 67 is aligned with the major axes of the elliptical electrodes. As in the previous embodiment, the surface distribution of perforations 49 is substantially uniform.

Figure 6:
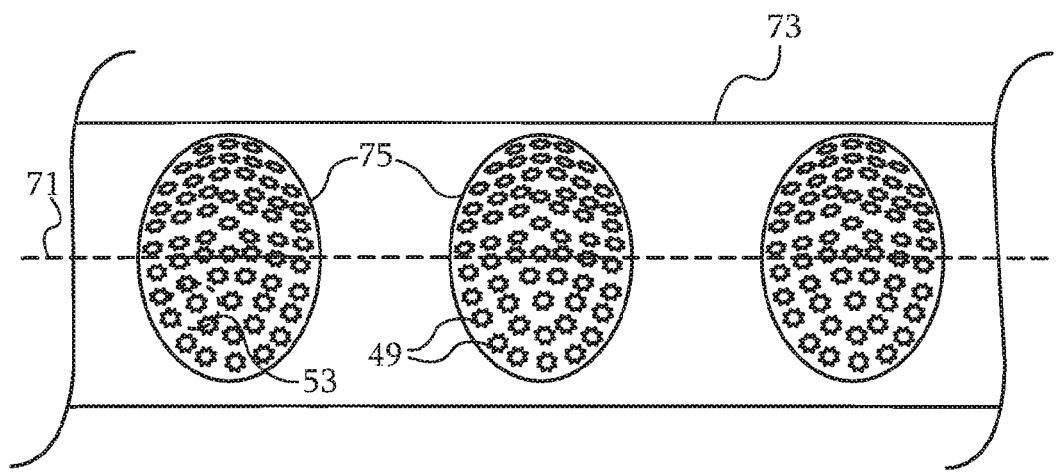
FIG. 6 is a fragmentary elevational view of the shaft of a catheter that is constructed and operative in accordance with an alternate embodiment of the invention.

Reference is now made to FIG. 6, which is a fragmentary elevational view of a shaft 73 of a catheter that is constructed and operative in accordance with an alternate embodiment of the invention. Electrodes 75 are elliptical in contour. The longitudinal axis 71 of the shaft 73 is aligned with the minor axes of the elliptical electrodes. As in the previous embodiments, the surface distribution of perforations 49 is substantially uniform.

Figure 7:
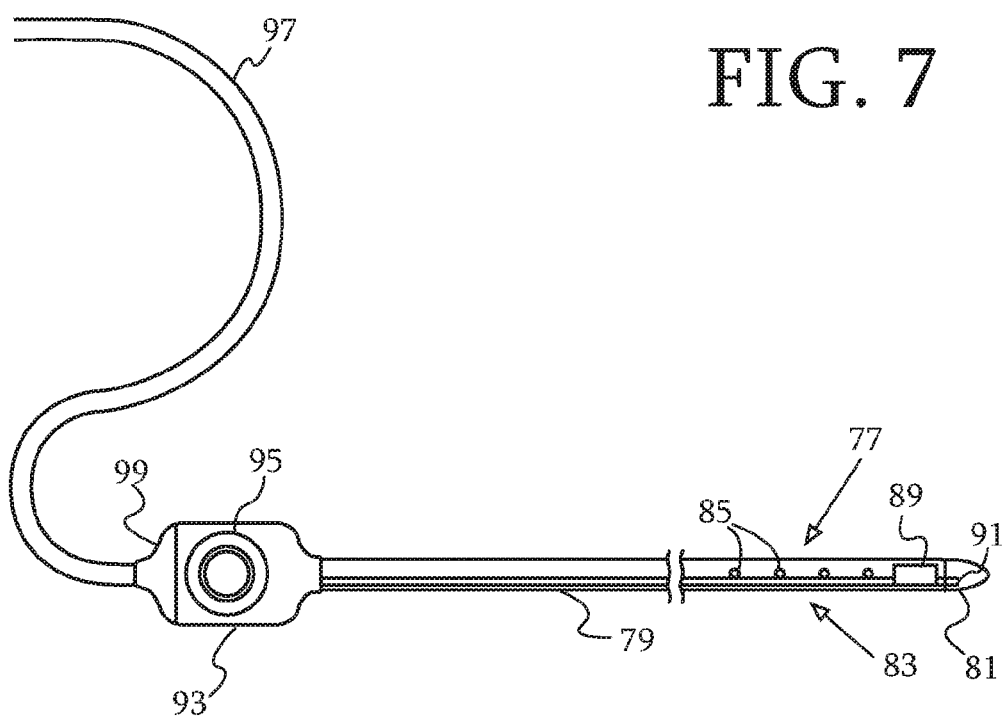
FIG. 7 is a schematic view of a cardiac catheter in accordance with an alternate embodiment of the invention.

The irrigated bump electrodes shown in the figure may also be arrayed along the length of catheters or probes of other types than lasso catheters. Reference is now made to FIG. 7, which is a schematic view of a cardiac catheter 77 in accordance with an alternate embodiment of the invention.

The catheter 77 includes a flexible body 79. An electrode 81 is at a distal portion 83 disposed for measuring the electrical properties of the heart tissue or for ablating defective cardiac tissue. The distal portion 83 further includes an array of non-contact electrodes 85 for measuring far field electrical signals in the heart chamber. The electrodes 85 may be constructed in accordance with any of the preceding embodiments. The details are not repeated in the interest of brevity.

An array 87 is a linear array in that the non-contact electrodes 38 are linearly arranged along the longitudinal axis of the distal portion 83. The distal portion 83 further includes at least one position sensor 89 that generates signals used to determine the position and orientation of the distal tip 91 within the body. The position sensor 89 is preferably adjacent to the tip 91. There is a fixed positional and orientational relationship of the position sensor 89, the tip 91 and the electrode 81.

A handle 93 of the catheter 14 includes controls 95 to steer or deflect the distal portion 83, or to orient it as desired. A cable 97 comprises a receptacle 99, which connects to the handle 93. The cable 97 may one or more isolation transformers (not shown), which electrically isolate the catheter 77 from the console 24 (FIG. 1). Alternatively, the isolation transformers may be contained in the receptacle 99 or in the system electronics of the console 24.

In embodiments in which there are three or more electrodes 85, they may be aligned as a single linear array along the shaft of the distal portion 83 as shown in FIG. 7.

Figure 8:
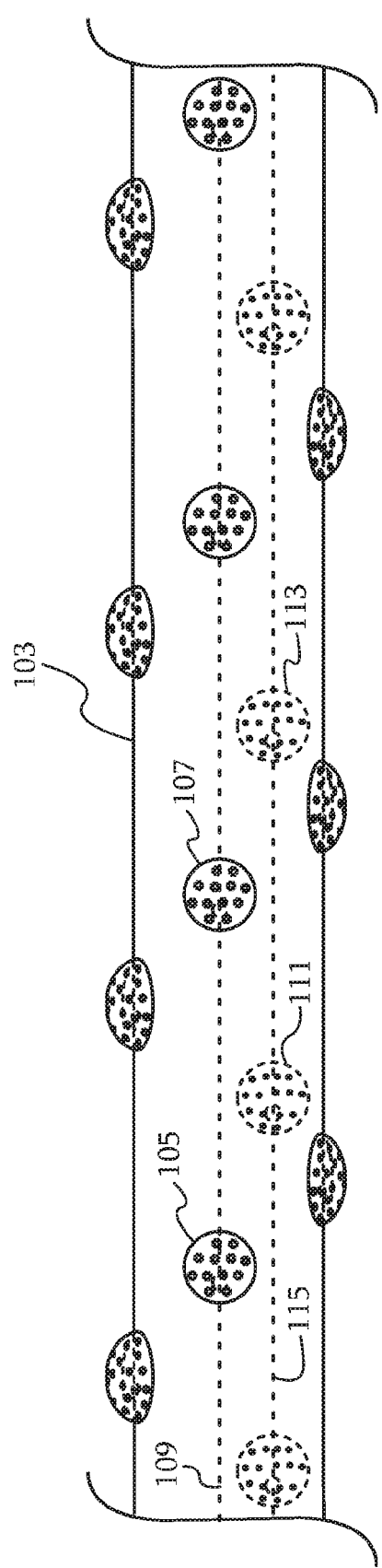
FIG. 8 is a fragmentary elevational view of a shaft of a catheter having a plurality of linear electrode arrays that is constructed and operative in accordance with an alternate embodiment of the invention.

Reference is now made to FIG. 8, which is a fragmentary elevational view of a shaft 103 of a catheter that is constructed and operative in accordance with an alternate embodiment of the invention. Alternatively, the electrodes 85 may be disposed as one or more arrays that spiral about the having circumferentially aligned or staggered electrodes that are distributed about the circumference of the shaft 103, and may forming a plurality of linear arrays. For example, as shown in FIG. 8, electrodes 105, 107 form a portion of a first linear array along broken line 109. Electrodes 111, 113 form a portion of a second linear array along broken line 115.

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

We claim:

1. A catheter, comprising:
   an insertion tube having a distal end; and
   a resilient distal section fixed to the distal end of the insertion tube, the distal section having an outer surface and an inner irrigating lumen and comprises a plurality of rounded cap-shaped electrodes that bulge above the outer surface covering substantially less than the circumference of the outer surface of the distal section, the electrodes each having a plurality of perforations formed therethrough, the outer surface being in fluid communication with the irrigating lumen via the perforations.

2. The catheter according to claim 1, wherein the insertion tube is configured for insertion through a blood vessel into a heart of a subject, and wherein the resilient distal section defines an open loop when deployed within the heart.

3. The catheter according to claim 2, wherein the open loop has a radius of between 7 mm and 15 mm.

4. The catheter according to claim 1, wherein the electrodes comprise at least three electrodes that are aligned as a linear array with a longitudinal axis of the distal section.

5. The catheter according to claim 1, wherein the electrodes comprise 1 and 50 perforations.

6. The catheter according to claim 1, wherein the electrodes comprise between 2 and 100 perforations.

7. The catheter according to claim 1, wherein the perforations of the electrodes measure between 0.05 mm and 0.4 mm in diameter.

8. The catheter according to claim 1, further comprising at least one electrically conductive wire that links the electrodes to a processor.

9. The catheter according to claim 1, wherein the electrodes bulge between 0.05 mm and 0.5 mm above the outer surface.

10. The cardiac catheter according to claim 1, wherein the electrodes are circular in contour.

11. The catheter according to claim 1, wherein the distal section has a longitudinal axis and wherein the electrodes are elliptical in contour.

12. The catheter according to claim 11, wherein the electrodes have respective major axes that are aligned with the longitudinal axis.

13. The catheter according to claim 11, wherein the electrodes have respective minor axes that are aligned with the longitudinal axis.

14. The catheter according to claim 1, further comprising a base section located between the proximal end of the resilient distal section and the distal end of the insertion tube said base section having a proximal end and a distal end and a multi-coil position sensor for generating second position and orientation dimensions.

15. The catheter according to claim 14, wherein the multi-coil position sensor is within 10 mm of the distal end of the base section.

16. A method for locating an arrhythmogenic area in a heart of a living subject, comprising the steps of:
inserting a catheter into a chamber of the heart, the catheter comprising an insertion tube having a distal end and a resilient distal section that has an outer surface and an inner irrigating lumen and is fixed to the distal end of the insertion tube and further comprises a plurality of electrodes that bulge above the outer surface, the electrodes having a plurality of perforations formed therethrough, the outer surface being in fluid communication with the irrigating lumen via the perforations;
locating the catheter in proximity to a target in the chamber;
analyzing electrical signals received from the target via the catheter to make a determination that the electrical signals are indicative of abnormal electrical conduction within the heart; and
responsively to the determination conducting energy into the heart to thereby affect the abnormal electrical conduction.

17. The method according to claim 16 further comprising passing a fluid through the irrigating lumen and the perforations of the electrodes while conducting the energy into the heart.

18. The method according to claim 16 further comprising the step of performing bi-polar ablation using two selected ones of the electrodes.

19. The method according to claim 16, wherein conducting the energy into the heart comprises pacing said heart by transmitting a pacing signal through the catheter.

20. The method according to claim 16, wherein and conducting the energy into the heart is performed until cardiac tissue within the target is ablated.

21. The method according to claim 16, wherein the resilient distal section is at least 1 mm in diameter.

22. The method according to claim 16, wherein when deployed in the heart, the distal section forms an open loop having a radius of between 7 mm and 15 mm.

23. The method according to claim 16, wherein the electrodes comprise at least three electrodes that are aligned as a linear array with a longitudinal axis of the distal section.

24. The method according to claim 16, wherein the electrodes comprise between 2 and 20 perforations.

25. The method according to claim 16, wherein the perforations of the electrodes measure between 0.1 mm and 0.4 mm in diameter.

26. The method according to claim 16, wherein the electrodes bulge between 0.1 mm and 0.5 mm above the outer surface.

27. The method according to claim 16, wherein the electrodes are circular in contour.

28. The method according to claim 16, wherein the distal section has a longitudinal axis and wherein the electrodes are elliptical in contour.

29. The method according to claim 28, wherein the electrodes have respective major axes that are aligned with the longitudinal axis.

30. The method according to claim 28, wherein the electrodes have respective minor axes that are aligned with the longitudinal axis.

31. The method according to claim 16, wherein the catheter further comprises a proximal base section having a multi-coil position sensor for generating second position and orientation dimensions.

32. The method according to claim 31, wherein the multi-coil position sensor is within 10 mm of the distal end of the base section.

* * * * *